(12) United States Patent
Lu (10) Patent No.: US 10,064,732 B2
(45) Date of Patent: Sep. 4, 2018

(54) ARTIFICIAL KNEE JOINT

(71) Applicant: UNITED ORTHOPEDIC CORPORATION, Hsinchu (TW)

(72) Inventor: Cheng-Kuang Lu, Hsinchu (TW)

(73) Assignee: UNITED ORTHOPEDIC CORPORTAION, Hsinchu (TW)

( * ) Notice: Subject to any disclaimer, the term of this patent is extended or adjusted under 35 U.S.C. 154(b) by 0 days.

(21) Appl. No.: 15/160,960

(22) Filed: May 20, 2016

(65) Prior Publication Data

US 2017/0231773 A1      Aug. 17, 2017

(30) Foreign Application Priority Data

Feb. 17, 2016   (TW) .............................. 105202293 U (51) Int. Cl.
*A61F 2/38*     (2006.01)

(52) U.S. Cl.
CPC .............. *A61F 2/384* (2013.01); *A61F 2/389* (2013.01); *A61F 2/3868* (2013.01); *A61F 2/3886* (2013.01)

(58) Field of Classification Search
CPC ........ A61F 2/385; A61F 2/3868; A61F 2/384; A61F 2/3836; A61F 2/3854; A61F 2/3859; A61F 2002/3863; A61F 2/3886; A61F 2/389; A61F 2002/30395; A61F 2002/30401

See application file for complete search history.

(56) References Cited

U.S. PATENT DOCUMENTS

| 4,219,893 A * | 9/1980 | Noiles ................... A61F 2/3836 623/20.25 |
| 6,773,461 B2 | 8/2004 | Meyers et al. |
| 8,328,873 B2 * | 12/2012 | Metzger .............. A61F 2/30721 623/20.28 |

* cited by examiner

*Primary Examiner* — Christopher D Prone
(74) *Attorney, Agent, or Firm* — Maschoff Brennan (57) ABSTRACT

The present invention provides an artificial joint, including a femur connecting device, a tibia connecting device, and a receiving device, wherein the femur connecting device is connected and fixed with the receiving device and the tibia connecting device via a fixing member unparallel to a joint-twisting axis, and wherein cushion member receives the femur connecting device via a pivot-receiving surface and receives the tibia connecting device via a twist-receiving surface, thereby providing an durable and reliable artificial joint.

10 Claims, 6 Drawing Sheets

FIG.6

ARTIFICIAL KNEE JOINT

FIELD OF THE INVENTION

The present invention relates to an artificial joint, and more particularly to an endurable and reliable artificial joint.

BACKGROUND OF THE INVENTION

Artificial joint is a kind of artifacts implanted into human body to replace natural human knee joint that becomes dysfunctional due to accidental injury, impairment or degeneration on account of fatigue, skeletal variations. There are various types of artificial joints, one of which is artificial hinge joint. Artificial hinge joint has been utilized since 1940s as an implant being implanted into human body to heal diseases such as bone defect or soft tissue dysfunctional.

A prior artificial hinge joint in the early years simply comprises a hinge component and a fixed bone shank, and has short service life. Since 1970s, the second generation of artificial hinge joint is made axially rotatable and used metal or polyethylene as bearing interface, which helps lengthen the service life of artificial joint. Since 1980s, the third generation of modularized artificial hinge joint has been developed by Stryker which further improves clinical effectiveness. However, since the third generation of artificial hinge joint still utilized hinge for transferring force in a way similar to the two previous generations, fracture problem still exists, in which plastic components near the hinge is still often easily broken and thus needs replacement.

Since 2000, some artificial joint manufacturers such as Zimmer Company (U.S. Pat. No. 6,773,461) revealed an artificial joint which reduces the bearing force of the hinge and further reduces the damage rate of plastic components. Moreover, since in this design, the axially rotatable hinge post combines with the hinge acting as a pivot during the implantation, the implant surgery can thus be performed in a less invasive way. However, in the above-mentioned model, the hinge post includes a screw thread parallel to the rotational direction of the artificial joint, causing the potential risk of the hinge post coining loose and falling off from the joint, which further causes the artificial joint to become ineffective.

SUMMARY OF THE INVENTION

Accordingly, an object of the present invention is to provide an endurable and reliable artificial joint to solve the problem in which the screw thread comes loose, causing the artificial joint to become ineffective.

To solve the problem in prior art, the present invention provides an artificial joint, comprising: a femur connecting device, including a femur implanting member and an assembly member, the femur implanting member being used to connect the artificial joint to a femur, the assembly member having a pivot portion and an assembly portion protruding downward from the pivot portion, and the pivot portion pivotally connecting to the femur implanting member in such a manner that the assembly member and the femur implanting member are mutually pivotable about a joint-pivoting axis, a tibia connecting device, including a base member and a tibia inserting member, wherein the tibia inserting member extends downward from the base member so as to connect to a tibia, and a receiving device, including an assembly base member and a cushion member, wherein the assembly base member is configured to be twistable relative to the base member along a joint-twisting axis perpendicular to the joint-pivoting axis, the assembly base member having an assembly-corresponding portion which is provided as matching the assembly portion at an upper side, the cushion member enclosing the assembly base member, and the cushion member having a pivot-receiving surface on an upper surface and a twist-receiving surface on a bottom surface, wherein the assembly portion is provided to connect to the assembly corresponding portion and a fixing part is provided to fix the assembly portion and the assembly corresponding portion at a place between the pivot-receiving surface and the twist-receiving surface in a fixing direction unparallel to the joint-twisting axis, thereby enabling the femur connecting device, the receiving device and the tibia connecting device to be connected together in such a manner that the femur connecting device and the tibia connecting device are mutually pivotable and twistable, and enabling the cushion member to receive the femur implanting member via the pivot-receiving surface and receive the base member via the twist-receiving surface.

In one embodiment of the present invention, the cushion member includes a protruded stopping portion at a front side of the pivot-receiving surface to limit the relative pivoting angle between the femur connecting device and the tibia connecting device.

In one embodiment of the present invention, the femur implanting member includes a fixed axial portion which is extended along the joint-pivoting axis, and the pivot portion of the assembly member is a sleeve tube which sleeves the fixed axial portion in such a manner that the assembly member and the femur implanting member are mutually pivotable.

In one embodiment of the present invention, the assembly portion is provided with an assembly hole parallel to the fixing direction, and the assembly corresponding portion includes a corresponding through hole which corresponds to the assembly hole in such a manner that the fixing part passes through the assembly hole and the corresponding through hole to fix the assembly portion and the assembly corresponding portion together.

In one embodiment of the present invention, the assembly base member is configured to be vertically movable with a small movement relative to the cushion member.

In one embodiment of the present invention, the fixing part is preset to be disposed in the assembly base member, and before the fixing part is located in the assembly portion, the fixing part is configured to fix the assembly base member with the cushion member in such a manner as to prevent vertical motion of the cushion member, the fixation between the assembly base member and the cushion member is released after the fixing part is located in the assembly portion.

In one embodiment of the present invention, the assembly portion of the assembly member is a non-circular column and the assembly corresponding portion is a recessed part in a manner that the assembly portion and the assembly corresponding portion are, after being combined together, in a mutually non-twistable state.

In one embodiment of the present invention, the artificial joint further comprises a reverse motion preventer provided at a back position behind the fixing part in the fixing direction in a manner that the reverse motion preventer prevents the fixing part from reversing along the fixing direction.

In one embodiment of the present invention, the assembly base member includes a twisting axial portion extending along the joint-twisting axis in which the twisting axial portion penetrates through the tibia connecting device in a manner that the assembly base member and the base member are mutually twistable.

In one embodiment of the present invention, the fixing direction is unparallel to the joint-pivoting axis.

Via the technical means of the present invention, the artificial joint of the present invention adopts newly developed hinge device which is applied to connect the upper surface and the bottom surface of the cushion member, and the joint-twisting axis is unparallel to the fixing direction, which solves the problem of the fixation being loose after long-term use, leading to the ineffectiveness of the artificial joint. Moreover, the pivot portion of the artificial joint of the present invention bears no burden from human body; instead, loadings caused by exertion or loadings borne by human body are transferred to the receiving device, thereby preventing early damage of the pivot portion due to stress concentration. Furthermore, the receiving device of the present invention is designed in a way that it receives the femur connecting device and the tibia connecting device via large contact area with good wear-resistance, thereby achieving a more stable structure and reducing the damage rate. Besides, the artificial joint of the present invention is easy to be assembled, and can thus lower both the time and difficulty of the implant surgery.

The preferred embodiments of the present invention are explained below with reference to appended drawings.

DETAILED DESCRIPTION OF THE PREFERRED EMBODIMENTS

The preferred embodiments of the present invention are described below with reference to FIG. 1 to FIG. 6. The description is only for explaining the preferred embodiments of the present invention, but not for limiting the implementation of the present invention.

Figure 1:
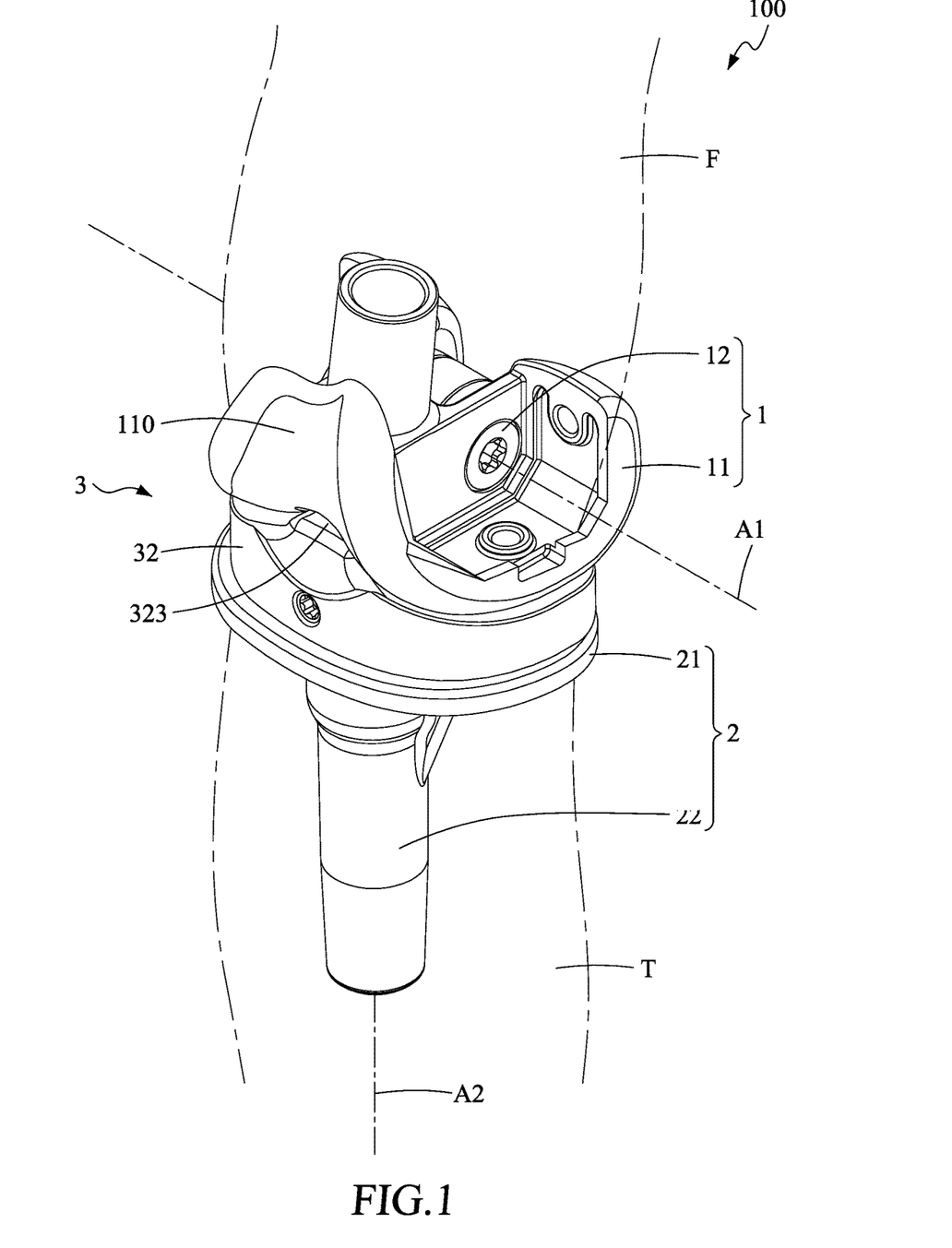
FIG. 1 is a stereogram illustrating an artificial joint according to one embodiment of the present invention.

As shown in FIG. 1, an artificial joint according to one embodiment of the present invention includes a femur connecting device 1, a tibia connecting device 2, and a receiving device 3.

Figure 2:
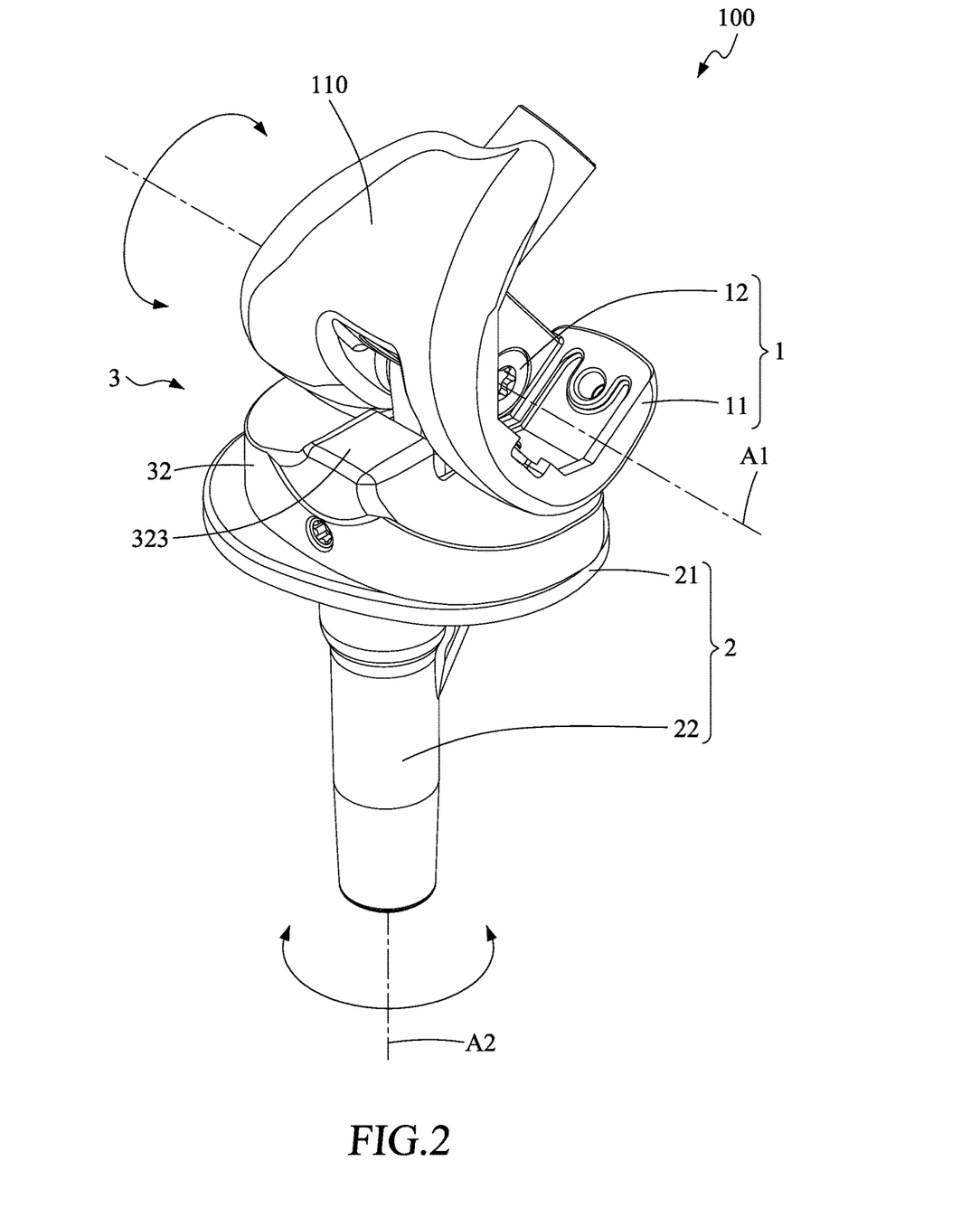
FIG. 2 is a stereogram illustrating the artificial joint of FIG. 1 pivoting and twisting.
Figure 3:
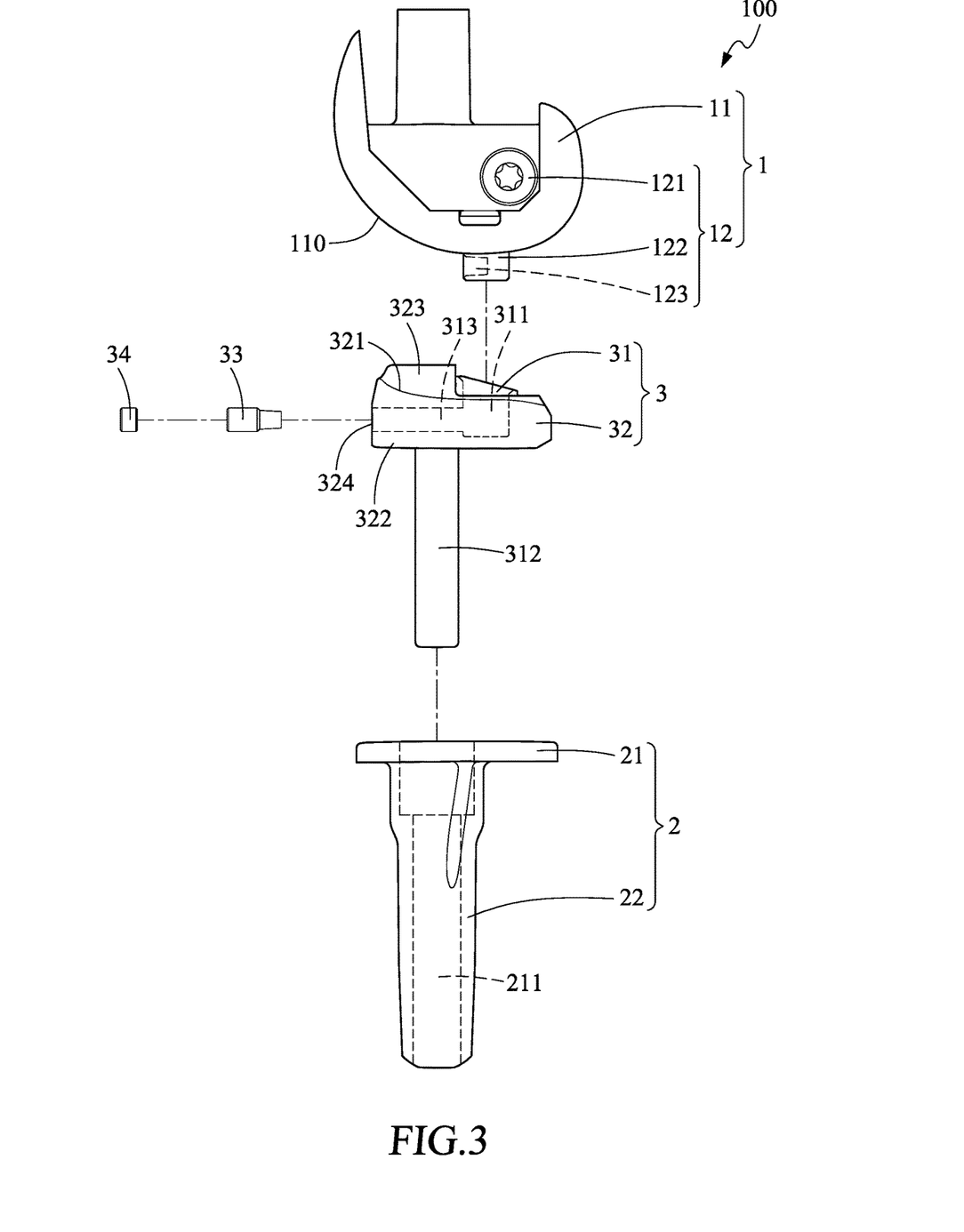
FIG. 3 is an explosion diagram illustrating the artificial joint according to the embodiment of the present invention.

As shown in FIG. 1 to FIG. 3, the femur connecting device 1 an upper part of the artificial joint 100 and comprises a femur implanting member 11 and an assembly member 12. The femur implanting member 11 is used to connect the artificial joint to a femur F, and is made to simulate the geometric structure of the femur. The femur implanting member 11 includes a smooth condyloid surface 110. The assembly member 12 includes a pivot portion 121 and an assembly portion 122 protruding downward from the pivot portion 121. The pivot portion 121 pivotally connecting to the femur implanting member 11 in such a manner that the assembly member 12 and the femur implanting member 11 are mutually pivotable about a joint-pivoting axis A1, simulating the flexion of knee joint.

As shown in FIG. 1 to FIG. 3, the tibia connecting device 2 is a lower part of the artificial joint 100, and comprises a base member 21 and a tibia inserting member 22, wherein the tibia inserting member 22 extends downward from the base member 21 so as to connect to a tibia T.

Figure 5:
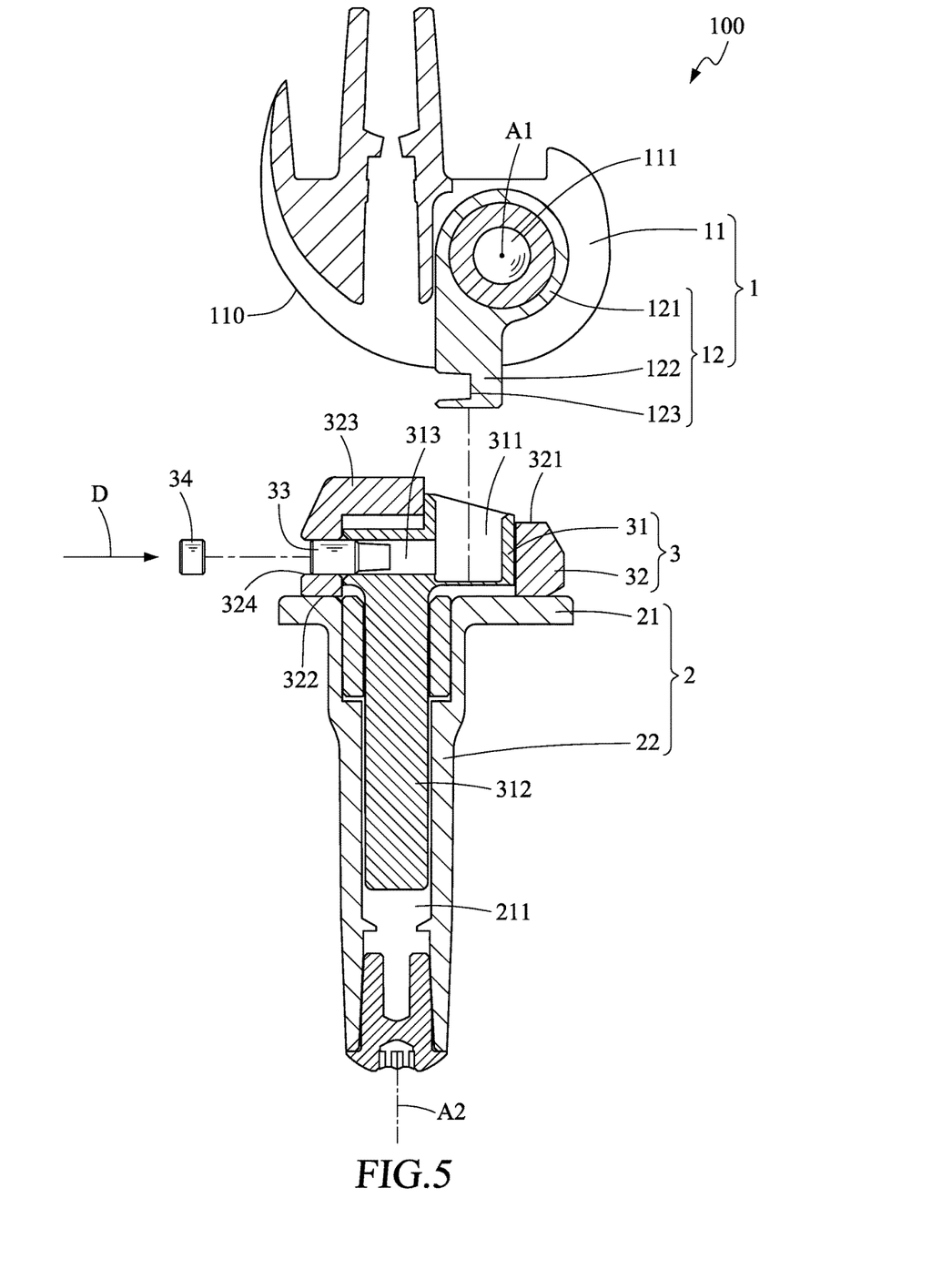
FIG. 5 is a sectional view illustrating the artificial joint according to the embodiment of the present invention before being assembled.
Figure 6:
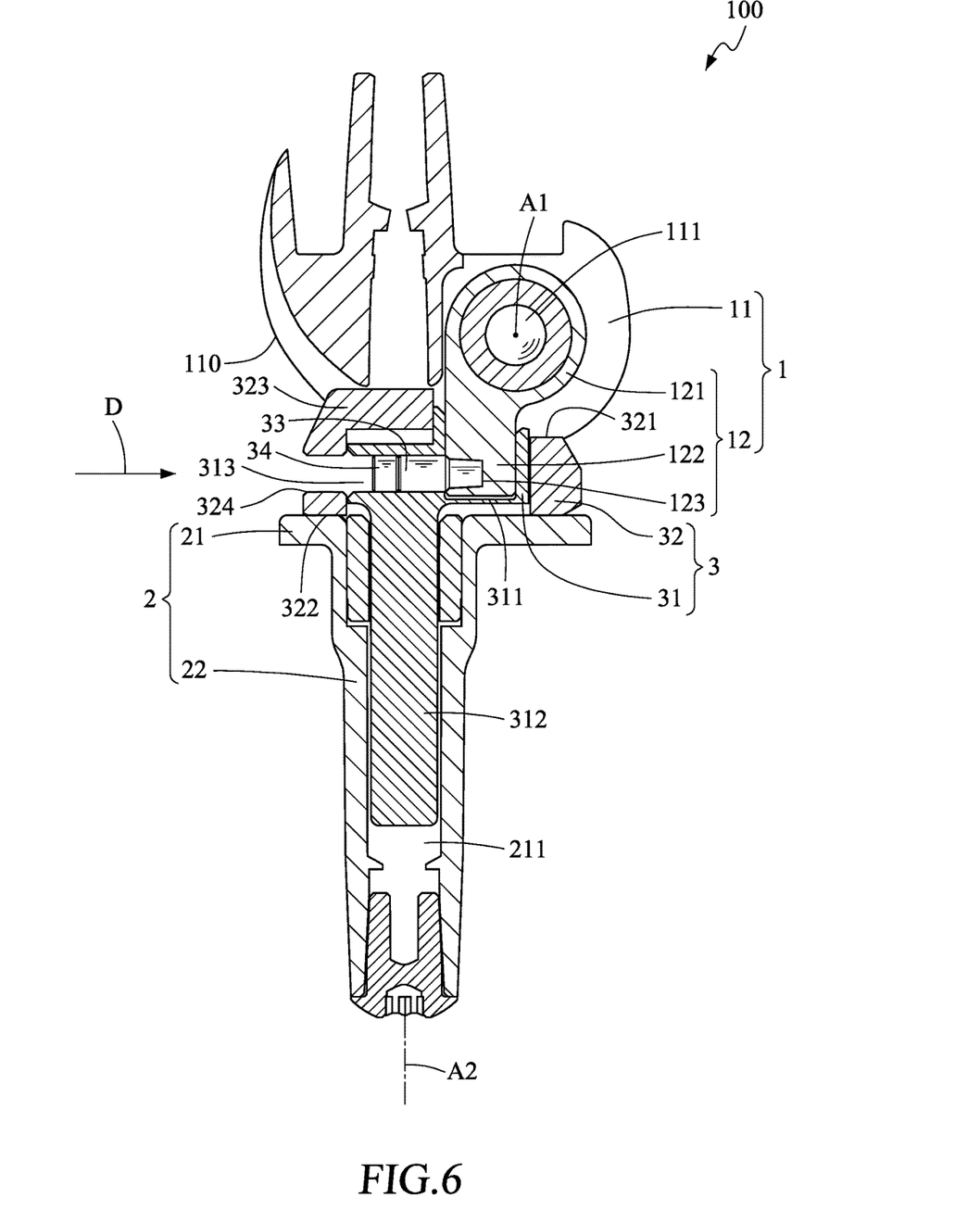
FIG. 6 is a sectional view illustrating the artificial joint according to the embodiment of the present invention after being assembled.

As shown in FIG. 1 and FIG. 3, the receiving device 3 is located between the femur connecting device 1 and the tibia connecting device 2 to receive the femur connecting device 1 and the tibia connecting device 2, in which the receiving device 3 includes an assembly base member 31 and a cushion member 32. The assembly base member 31 is configured to be twistable relative to the base member 21 along a joint-twisting axis A2 perpendicular to the joint-pivoting axis A1 so as to simulate the axial rotation of knee joint. The assembly base member 31 has an assembly-corresponding portion 311 which is provided as matching the assembly portion 122 of the femur connecting device 1 at an upper side so as to connect with the assembly portion 122. The cushion member 32 encloses the assembly base member 31, the cushion member 32 having a pivot-receiving surface 321 on an upper surface and a twist-receiving surface 322 on a bottom surface As shown in FIG. 5 and FIG. 6, the assembly portion 122 of the femur connecting device 1 is provided to connect to the assembly corresponding portion 311 of the receiving device 3 and a fixing part 33 is provided to fix the assembly portion 122 and the assembly corresponding portion 311 at a place between the pivot-receiving surface 321 and the twist-receiving surface 322 in a fixing direction D unparallel to the joint-twisting axis A2, thereby enabling the femur connecting device 1, the receiving device 3 and the tibia connecting device 2 to be connected together.

As to the structure between the femur connecting device 1, the receiving device 3, and the tibia connecting device 2, via the mutually pivotable structure between the assembly member 12 and the femur implanting member 11, and via the mutually twistable structure between the assembly base member 31 and the base member 21, the femur connecting device 1 and the tibia connecting device 2 are mutually twistable and pivotable. Besides, since the fixing direction D of the fixing part 33 and the joint-twisting axis A2 are not in the same direction, the vibration caused by the artificial joint 100 motion will not be transferred and thus will not affect the structure of the artificial join 100, which reduces the possibility that the fixing part 33 becomes loose after long-term use, which leads to the ineffectiveness of the artificial joint 100. Furthermore, in other embodiments, the fixing direction D is further unparallel to the joint-pivoting axis A1. Preferably, the fixing direction is perpendicular to the joint-pivoting axis A1 and the joint-twisting axis A2, as in the present embodiment, by which the problem of components falling off and not running well is solved.

Furthermore, concerning the structure between the femur connecting device1, the receiving device 3, and the tibia connecting device 2, for the femur connecting device 1, or to say, a platform surface at a bottom side of the condyloid surface 110, to contact the cushion member 32, the cushion member 32 receives the femur implanting member 11 via the pivot-receiving surface 321, and the cushion member 32 receives the twist-receiving surface 322 via the base member 21. By the above-mentioned means, loadings caused by exertion or loadings borne by human body will not be directly transferred to the pivot portion 121. Instead, these loadings are transferred to the cushion member 32 by the femur F via the pivot-receiving surface 321 so as to prevent early damage of the pivot portion 121 due to stress concentration. Besides, the pivot-receiving surface 321 and the twist-receiving surface 322 of the cushion member 32 is equipped with large contact area with good wear-resistance, thereby achieving a more stable structure and reducing the damage rate.

As shown in FIG. 1 to FIG. 3, the cushion member 32 includes a protruded stopping portion 323 at a front side of the pivot-receiving surface 321, i.e. the side nearest the knee, to limit the relative pivoting angle between the femur connecting device 1 and the tibia connecting device 2. More specifically, the stopping portion 323 is a protruded platform body integrally formed with the cushion member 32, whose shape corresponds to the platform surface at the bottom side of the condyloid 110 of femur implanting member 11. The height of the stopping portion 323 is such that the stopping portion 323 will press against the platform surface so as to avoid hyperextension of the artificial knee 100.

Figure 4:
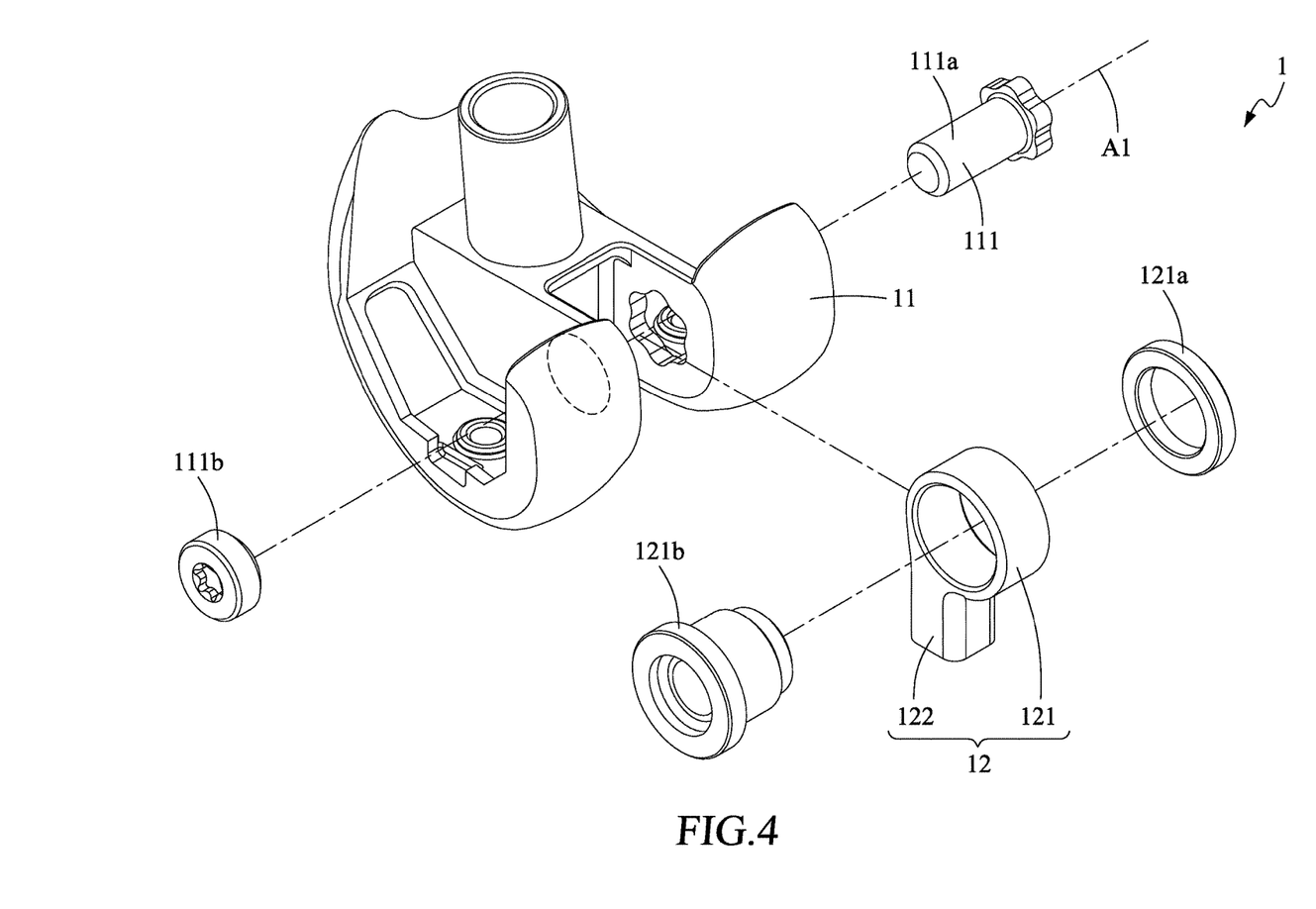
FIG. 4 is an explosion diagram illustrating a femur connecting device according to the embodiment of the present invention.

As shown in FIG. 4, according to the present embodiment, the femur implanting member 11 includes a fixed axial portion 111 which is extended along the joint-pivoting axis A1. The fixed axial portion 111 is formed by an axial post 111a and an end cap 111b which are sleeved together, and is fixed together with the femur implanting member 11 without the femur implanting member 11 and the fixed axial portion 111 being mutually rotatable. In this embodiment, an end of the fixed axial portion 111 is in a non-circular shape, a six-petal flower shape in this embodiment, so that the fixed axial portion 111 is fixed to the femur implanting member 11 in a way that the fixed axial portion 111 and the femur implanting member 11 is mutually non-rotatable. The pivot portion 121 of the assembly member 12 is a sleeve tube which sleeves the fixed axial portion 111 in such a manner that the assembly member 12 and the femur implanting member 11 are mutually pivotable. Moreover, a packing ring is disposed between the sleeve tube and the fixed axial portion 111 so as to facilitate the mutual rotation of the sleeve tube and the fixed axial portion 111. In this embodiment, the packing ring is composed of components 121a and 121b. Preferably, the packing ring is made of plastic so as to avoid the production of metal scraps caused by relative motions between metal components and to thus reduce the risk of complications. Besides, using plastic as the material of the packing ring reduces the frictional force between metal components, thereby facilitating the motion of the artificial knee. This kind of pivot structure with fixed axis utilizes the contact of the inner surface of the packing ring and the outer surface of the fixed axial portion 111 to bear the frictional force caused by rotation, which is a more durable way than the pivot structure with rotating axle, in which the two ends of the rotating axle bear the frictional force caused by rotation and in which the rotating axle is thereby inclined to fall off.

As shown in FIG. 3, in the receiving device 3 of the present embodiment, the assembly member 31 includes a twisting axial portion 312 extending along the joint-twisting axis A2. The tibia connecting device 2 is provided with a receiving through hole 211 extended along the joint-twisting axis A2. The twisting axial portion 312 passes through the receiving through hole 211 so as to make the assembly base member 31 and the base member 21 mutually twistable. Certainly, the present invention is not limited to this. In other embodiments, the assembly base member 31 and the base member 21 can be mutually twistable via other structural means.

As shown in FIG. 3, the assembly portion 122 of the assembly member 12 is a non-circular column and the assembly corresponding portion 311 is a recessed part in a manner that the assembly portion 122 and the assembly corresponding portion 311 are, after being combined together, in a mutually non-twistable state. Furthermore, as shown in FIG. 5 and FIG. 6, the assembly portion 122 is provided with an assembly hole 123 parallel to the fixing direction D, and the assembly corresponding portion 311 includes a corresponding through hole 313 which is located at a position between the pivot-receiving surface 321 and the twist-receiving surface 322 and communicates with the assembly corresponding portion 311 and corresponds to the assembly hole 123 in such a manner that the fixing part 33 passes through the corresponding through hole 313 and the assembly hole 123 so as to fix the assembly portion 123 and the assembly corresponding portion 311 together. Besides, in this embodiment, the cushion member 32 includes a through hole 324 corresponding to the assembly corresponding through hole 313 so that the fixing part 33 passes through the through hole 324 and the corresponding through hole 313, with the front end of the fixing part 33 contacting the assembly portion 123 and stuck on the inner cone surface of the assembly portion 123, and thus locking the assembly portion 123 and the assembly corresponding portion 311.

As shown in FIG. 5 and FIG. 6, the fixing part 33 is preferably a screw so as to fix the assembly portion 122 and the assembly corresponding portion 311 together via screw fixation. Certainly, the present invention is not limited to this. In other embodiments, the fixing part is a hook ring, and the assembly portion and the assembly corresponding portion are a concaved slot via which the hook ring is fastened to the concaved slot in such a manner that the assembly portion and the assembly corresponding portion are fixed together.

Moreover, the artificial joint 100 further comprises a reverse motion preventer 34, provided at a back position behind the fixing part 33 in the fixing direction D in a manner that the reverse motion preventer prevents the fixing part from reversing along the fixing direction. For instance, the reverse motion preventer 34 is a screw located at a back position behind the fixing part 33 in the corresponding through hole 313, and by utilizing the pushing force in the fixing direction D between the reverse motion preventer 34 and the fixing part 33, the frictional force between the screw thread of the fixing part 33 and the reverse motion stopper 34 and prevents reverse motion.

As shown in FIG. 5 or FIG. 6, the cushion member 32 in the receiving device 3 is configured to be vertically movable with a small movement relative to the assembly base member. More specifically, cushion member 32 does not closely enclose the assembly base member 31; instead, there is a space between the cushion member 32 and the assembly base member 31 that allows slight amount of movements of the assembly base member 31 so as to render the artificial joint 100 more similar to human knee joint.

Furthermore, since the assembly base member 31 being slightly movable relative to the cushion member 32 renders the disposition of the fixing part 33 inconvenient, which happens in surgery such as joint replacement, the fixing part 33 is preferably preset to be disposed in the assembly base member 31, and before the fixing part 33 is located in the assembly portion 122, the fixing part 33 is configured to fix the assembly base member 31 with the cushion member 32 in such a manner as to prevent vertical motion of the cushion member 32, the fixation between the assembly base member 31 and the cushion member 32 is released after the fixing part 33 is located in the assembly portion 122. For example, as shown in FIG. 5, when in a preset position, one end of the fixing part 33 is located in the corresponding through hole 313 of the assembly base member 31 while another end of the fixing part is located in the through hole 324 of the cushion member 32 in such a manner that the assembly base member 31 and the cushion member 32 are fixed together and is not mutually movable. As shown in FIG. 6, after one end of the fixing part 33 reaches the assembly portion 122, the other end of the fixing part 33 leaves the through hole 324 of the cushion member 32, thereby releasing the fixation.

The above description is only an explanation of the preferred embodiment of the present invention. A person with ordinary skill in the art can make various modifications to the present invention based on the scope of the claims and the above description. However, those modifications shall fall within the scope of the present invention.

What is claimed is:

1. An artificial joint, comprising:
a femur connecting device, including a femur implanting member and an assembly member, the femur implanting member being capable of connecting the artificial joint to a femur, the assembly member having a pivot portion and an assembly portion protruding downward from the pivot portion, and the pivot portion pivotally connecting to the femur implanting member in such a manner that the assembly member and the femur implanting member are mutually pivotable about a joint-pivoting axis;
a tibia connecting device, including a base member and a tibia inserting member, wherein the tibia inserting member extends downward from the base member so as to be capable of being connected to a tibia;
a receiving device, including an assembly base member and a cushion member, wherein the assembly base member is configured to be twistable relative to the base member along a joint-twisting axis perpendicular to the joint-pivoting axis, the assembly base member having an assembly-corresponding portion which is provided as matching the assembly portion at an upper side, the cushion member enclosing the assembly base member, and the cushion member having a pivot-receiving surface on an upper surface and a twist-receiving surface on a bottom surface; and
a fixing part being an individual member independent of the femur connecting device, the receiving device and the tibia connecting device, and the fixing part moving with respect to the femur connecting device, the receiving device and the tibia connecting device along a fixing direction nonparallel to the joint-twisting axis, such that the fixing part fixes the assembly portion and the assembly corresponding portion in a manner that the fixing part is located at a place between the pivot-receiving surface and the twist-receiving surface, wherein the assembly portion and the assembly corresponding portion do not twist relative to each other after being connected, thereby enabling the femur connecting device, the receiving device and the tibia connecting device to be connected together in such a manner that the femur connecting device and the tibia connecting device are mutually pivotable and twistable, and enabling the cushion member to receive the femur implanting member via the pivot-receiving surface and receive the base member via the twist-receiving surface.

2. The artificial joint as claimed in claim 1, wherein the cushion member includes a protruded stopping portion at a front side of the pivot-receiving surface to limit the relative pivoting angle between the femur connecting device and the tibia connecting device.

3. The artificial joint as claimed in claim 1, wherein the femur implanting member includes a fixed axial portion which is extended along the joint-pivoting axis, and the pivot portion of the assembly member is a sleeve tube which sleeves the fixed axial portion in such a manner that the assembly member and the femur implanting member are mutually pivotable.

4. The artificial joint as claimed in claim 1, wherein the assembly portion is provided with an assembly hole parallel to the fixing direction, and the assembly corresponding portion includes a corresponding through hole which corresponds to the assembly hole in such a manner that the fixing part passes through the assembly hole and the corresponding through hole to fix the assembly portion and the assembly corresponding portion together.

5. The artificial joint as claimed in claim 1, wherein the assembly base member is configured to be vertically movable with a movement relative to the cushion member.

6. The artificial joint as claimed in claim 5, wherein the fixing part is preset to be disposed in the assembly base member, and before the fixing part is located in the assembly portion, the fixing part is configured to fix the assembly base member with the cushion member in such a manner as to prevent vertical motion of the cushion member, the fixation between the assembly base member and the cushion member is released after the fixing part is located in the assembly portion.

7. The artificial joint as claimed in claim 1, wherein the assembly portion of the assembly member comprises a non-circular column and the assembly corresponding portion comprises a recessed part.

8. The artificial joint as claimed in claim 1, further comprising a reverse motion preventer provided at a back position behind the fixing part in the fixing direction in a manner that the reverse motion preventer prevents the fixing part from reversing along the fixing direction.

9. The artificial joint as claimed in claim 1, wherein the assembly base member includes a twisting axial portion extending along the joint-twisting axis in which the twisting axial portion penetrates through the tibia connecting device in a manner that the assembly base member and the base member are mutually twistable.

10. The artificial joint as claimed in claim 1, wherein the fixing direction is unparallel to the joint-pivoting axis.

* * * * *